(12) United States Patent
Gaschino et al.

(10) Patent No.: US 6,325,821 B1
(45) Date of Patent: Dec. 4, 2001

(54) STENT FOR ANGIOPLASTY

(75) Inventors: Paolo Gaschino; Giovanni Rolando, both of Chivasso (IT)

(73) Assignee: Sorin Biomedica Cardio S.p.A. (IT)

( * ) Notice: Subject to any disclaimer, the term of this patent is extended or adjusted under 35 U.S.C. 154(b) by 0 days.

(21) Appl. No.: 09/069,425

(22) Filed: Apr. 29, 1998

(30) Foreign Application Priority Data

Apr. 29, 1997 (IT) ................................. TO97A0369

(51) Int. Cl.⁷ ............................ A61F 2/06; A61M 29/00
(52) U.S. Cl. ........................................ 623/1.15; 606/194
(58) Field of Search .......................... 623/1, 1.15, 1.16, 623/1.13, 1.14, 1.1, 1.12, 1.2, 1.18, 1.19, 135; 606/194, 192

(56) References Cited

U.S. PATENT DOCUMENTS

| | | |
|---|---|---|
| 4,503,569 | 3/1985 | Dotter . |
| 4,768,507 | 9/1988 | Fischell et al. . |
| 4,776,337 | 10/1988 | Palmaz . |
| 4,800,882 | 1/1989 | Gianturco . |
| 4,830,003 | 5/1989 | Wolff et al. . |
| 4,856,516 | 8/1989 | Hillstead . |
| 4,886,062 | 12/1989 | Wiktor . |
| 4,907,336 | 3/1990 | Gianturco . |
| 5,421,955 | 6/1995 | Lau et al. . |
| 5,449,373 | * 9/1995 | Pinchasik et al. ................... 606/198 |

(List continued on next page.)

FOREIGN PATENT DOCUMENTS

| | | |
|---|---|---|
| 297 01 758 U1 | 5/1997 | (DE) . |
| 297 02 671 U1 | 5/1997 | (DE) . |
| A-0 201 466 | 11/1986 | (EP) . |
| 0 873 728 A2 | 10/1998 | (EP) . |
| 0 873 729 A2 | 10/1998 | (EP) . |
| 0 903 123 A1 | 3/1999 | (EP) . |
| TO96A000655 | 7/1996 | (IT) . |
| WO 9603092 A1 | 2/1996 | (WO) . |
| WO 97/32544 | 9/1997 | (WO) . |
| WO 97/33534 | 9/1997 | (WO) . |
| WO 98/30172 | 7/1998 | (WO) . |
| WO 99/15108 | 1/1999 | (WO) . |
| WO 00/02502 | 1/2000 | (WO) . |
| WO 00/06051 | 2/2000 | (WO) . |

OTHER PUBLICATIONS

Topol, *Textbook of Interventional Cardiology*, Second Edition, vol. 2, pp. 687–815 (1994).

English language abstract of Italian Patent Application No. TO96A000655.

European Search Report on European Patent Application No. EP 98 10 7382, including annex, dated Sep. 7, 1998, 2 pages.

* cited by examiner

*Primary Examiner*—David H. Willse
*Assistant Examiner*—Alvin Stewart
(74) *Attorney, Agent, or Firm*—Popovich & Wiles, P.A.

(57) ABSTRACT

A stent for angioplasty has a body (1) in the form of a generally tubular envelope susceptible of being dilated in use from a radially-contracted position into a radially-expanded position. The body of the stent (1) includes a plurality of successive segments (2) having a serpentine shape with loop parts having sequentially-opposite concavity. These loop parts are connected by connector parts (4) and the bridges (3) which connect the segments (2) of the stent together join to the aforesaid connector parts (4).

35 Claims, 3 Drawing Sheets

U.S. PATENT DOCUMENTS

| | | |
|---|---|---|
| 5,514,154 | 5/1996 | Lau et al. . |
| 5,569,295 | 10/1996 | Lam . |
| 5,591,197 | 1/1997 | Orth et al. . |
| 5,603,721 | 2/1997 | Lau et al. . |
| 5,649,952 | 7/1997 | Lam . |
| 5,681,346 | 10/1997 | Orth et al. . |
| 5,695,516 | 12/1997 | Fischell et al. . |
| 5,697,971 | 12/1997 | Fischell et al. . |
| 5,718,713 | 2/1998 | Frantzen . |
| 5,725,572 | 3/1998 | Lam et al. . |
| 5,728,131 | 3/1998 | Frantzen et al. . |
| 5,728,158 | 3/1998 | Lau et al. . |
| 5,733,303 | 3/1998 | Israel et al. . |
| 5,733,330 | 3/1998 | Cox . |
| 5,735,893 | 4/1998 | Lau et al. . |
| 5,741,327 | 4/1998 | Frantzen . |
| 5,755,776 | 5/1998 | Al-Saadon . |
| 5,759,174 | 6/1998 | Fischell et al. . |
| 5,759,192 | 6/1998 | Saunders . |
| 5,766,238 | 6/1998 | Lau et al. . |
| 5,766,239 | 6/1998 | Cox . |
| 5,769,887 | 6/1998 | Brown et al. . |
| 5,776,161 * | 7/1998 | Globerman ............... 606/194 |
| 5,776,183 | 7/1998 | Kanesaka et al. . |
| 5,807,404 * | 9/1998 | Richter ..................... 623/1 |
| 5,827,321 * | 10/1998 | Roubin et al. ............ 606/195 |
| 6,033,433 * | 3/2000 | Ehr et al. .................. 623/1 |

STENT FOR ANGIOPLASTY

FIELD OF THE INVENTION

The present invention generally concerns stents for angioplasty.

BACKGROUND OF THE INVENTION

The term "stent" is intended to indicate in general those devices intended for endoluminal application (for example, in a blood vessel), usually effected by means of catheterization, with subsequent deployment in place so as to achieve local support of the lumen. The primary purpose of this is to eliminate and avoid the restenosis of the treated area. It is moreover noted that it has already been proposed in the art to use substantially similar structures in order to achieve the deployment and anchorage in situ of vascular grafts; naturally, this possible extension of the field of application is also to be understood as being included within the scope of the invention.

For a general review of vascular stents, reference may usefully be made to the work "Textbook of Interventional Cardiology" edited by Eric J Topol, W. B. Saunders Company, 1994 and, in particular, to section IV of volume II, entitled "Coronary Stenting".

Many patent documents have addressed this issue as shown, for example, by U.S. Pat. No. 4,503,569; U.S. Pat. No. 4,768,507; U.S. Pat. No. 4,776,337; U.S. Pat. No. 4,800,882; U.S. Pat. No. 4,830,003; U.S. Pat. No. 4,856,516; U.S. Pat. No. 4,886,062; U.S. Pat. No. 4,907,336; and EP-A-0 201 466.

Notwithstanding the extensive research and experimentation, as documented at the patent level, only a relatively small number of operative solutions have, until now, found practical application. This is due to various factors, among which the following problems or requirements may be mentioned:

- ensuring that, while moving towards the treatment site, the stent is capable of adapting with sufficient malleability to the path taken, even as regards less curved sections such as those which may exist, for example, in some peripheral vessels; all of this without detrimentally affecting the ability of the stent to provide an effective support action once positioned and deployed;
- avoiding, or at least limiting, the longitudinal shortening effect which occurs in many stents on deployment,
- achieving the maximum homogeneity and uniformity in the expansion movement, avoiding (when this is not a required effect) a situation in which this movement manifests itself to an extent and at times which vary in different areas or sections of the stent;
- providing the wall of the lumen which is being supported with a support surface that is as extensive as possible;
- avoiding the origination of complex shapes and/or possible stagnation sites susceptible, especially in blood vessels, of giving rise to negative phenomena such as coagulation, thrombosis, etc.; and
- reconciling the requirements described above with the modality and criteria of simple production, reliability and the introduction of currently available technology.

The present invention, having the characteristics referred to specifically in the following claims, has the object of resolving, at least in part, the problems outlined above. To this end, the solution according to the present invention is capable of being integrated with at least some of the solutions described in co-pending U.S. patent application Ser. Nos. 08/964,158; 08/987,365; 08/997,597; 09/004,376, each of which are hereby incorporated by reference, and in the Italian patent application No. TO96A000655 all of which are assigned to the same assignee of the present application.

SUMMARY OF THE INVENTION

This invention is a stent for angioplasty comprising a body (1) in the form of a generally tubular envelope capable of being dilated from a radially-contracted position to a radially-expanded position, wherein the body includes a plurality of successive segments (2) having a serpentine-like shape with opposite loop parts in sequence; the loop parts being connected by connector parts (4); and the successive segments (2) are connected to each other by bridge elements (3) joined to the connector parts (4). The bridge elements may have an inflexible median portion and/or a general V-shape. In preferred embodiments, the bridge elements are convex along the periphery of the stent or have opposite, sequential convexity along the periphery of the stent. When the stent is in the radially-contracted position, the connector parts (4) may extend in a generally longitudinal direction (z) with respect to the stent; and the bridge elements (3) may have end parts (3a) which, when the stent is in the radially-contracted position, extend in a transverse direction with respect to the stent.

In another preferred embodiment, the connector parts (4) may extend in a generally oblique direction with respect to the longitudinal axis of the stent and are substantially unchanged following the dilatation of the stent from the radially-contracted position to the radially-expanded position.

Further, the bridge elements (3) may have end parts (3a) joined to the connector parts (4) in a generally oblique direction with respect to the longitudinal axis of the stent (1), these also being substantially unchanged following the dilatation of the stent. At least some of the connector parts (4) may be joined to associated pairs of bridge elements (3) connecting successive segments (2) in the plurality in a general cross-shape. In the radially-contracted position, the loop parts may have apex parts (2a) which extend along an approximately lobe-shape path.

BRIEF DESCRIPTION OF THE DRAWINGS

The invention will now be described, purely by way of non-limitative example, with reference to the accompanying drawings in which.

Figure 1:
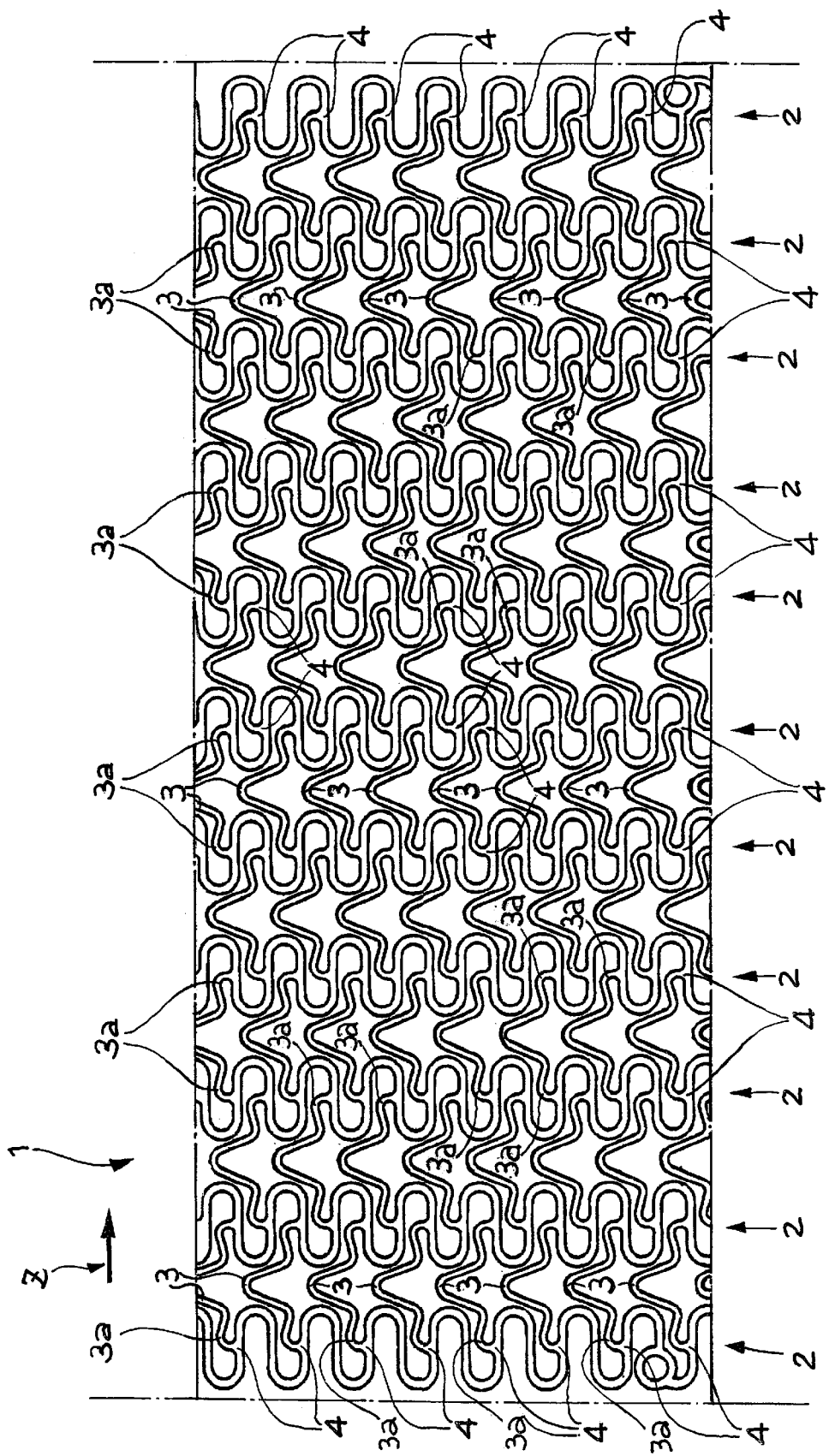
FIG. 1 illustrates, in a theoretical plane, the geometrical characteristics of the wall of a stent for angioplasty manufactured according to the invention, illustrated in the radially-contracted position.

The reference numeral 1 is utilised in the drawings to indicate in its entirety a stent for angioplasty. For a general identification of the manner of use and the characteristics of this implantation device, reference should be made to the documentation listed in the Background of the Invention.

DETAILED DESCRIPTION OF THE PREFERRED EMBODIMENTS

By way of summary, it will be recalled that the stent 1 is usually formed as a body which is a tubular envelope generally between several millimeters and several tens of millimeters in length, and with a wall thickness (the wall usually being an apertured mesh or loop structure, as will be seen better below) of the order of, for example, several hundredths of millimeters, because of its possible insertion into a lumen (such as a blood vessel) at a site where stenosis is to be corrected. The stent is normally located in situ by means of catheterization followed by radial expansion from an introduction diameter of the order of, for example, 1.5–1.8 mm, to an expanded diameter of the order of, for example, 3–4 mm such that, in this expanded condition, the stent exerts a supporting action on the lumen, eliminating and avoiding restenosis. In general, the external diameter in the radially-contracted condition is chosen so as to enable the introduction of the stent into the lumen being treated, while the expanded diameter corresponds in general to the diameter required to be maintained in the lumen once the stenosis has been eliminated. It should also be remembered that, although the principle application of the stent described is in relation to the treatment of blood vessels, its use as a support element for any lumen present in the human or animal body can be envisaged (and is therefore included in the scope of this invention).

As regards the modality and the criteria which enable the deployment (that is, the in situ expansion) of the stent, currently the most widely used solution is to use a so-called balloon catheter, disposing the stent about the balloon of the catheter in the contracted condition and then expanding the balloon once the stent has been taken to the deployment site. Different solutions are also possible, such as using superelastic materials which, once the containment elements intended to hold the stent in the contracted condition until it has reached the implantation site are removed, give rise to the expansion of the stent. In addition, or alternatively, it has been suggested that materials having a so-called "shape memory" may be used so as to achieve the radial expansion in the implant position.

Usually (for more precise details, reference should be made to the bibliographic and patent documentation listed in the introduction to the description), the stent is made from a metal capable of satisfying two fundamental requirements of use, that is, the capability of plastically deforming during the expansion phase and the capability of resisting, and thus retaining the expanded shape, possible forces which would otherwise lead to the stent re-closing. The material known under the commercial name "Nitinol" has been shown to be successful both from the point of view of its superelasticity, and its shape memory which is possibly needed during the expansion phase.

In any case, these technological aspects will not be dealt with in detail in the present description in that they are not in themselves relevant to the comprehension and production of the invention. This also applies essentially to the technology for the production of the stent according to the invention. As has already been said, these stents assume, in general terms, the form of a body made from a tubular envelope with an apertured wall. As regards production, reference may be made, using known techniques, to at least three basic arrangements, which are:

forming the stent from a continuous tubular blank intended to be segmented into individual stents, with the apertured parts being formed using techniques such as laser incision, photo-incision, electroerosion, etc.;

forming the stent from a strip-like body in which the apertured zones are formed, for example, using the techniques listed above, with the subsequent closure of the strip-like element into a tube; and forming the stent from metal wire shaped by the subsequent attachment of wire loops, for example, using operations of micro welding, brazing, gluing, crimping, etc.

The first arrangement described is the one currently preferred by the Applicant for producing stents according to the embodiments described below. In particular, cutting using laser beams has been shown to be the most flexible solution as regards the possibility of the rapid modification of the characteristics of the stent during production, in response to specific applicational requirements.

In any case, it is emphasized that even this aspect of production is not relevant, in that it is marginal, to the production of the invention. This also applies to the choice of the individual techniques and the order in which the various operations described (the production of the apertured parts, segmentation, possible folding of the strip-like element, etc.) are performed.

In the embodiments illustrated here, the body of the stent 1 extends longitudinally in the direction generally identified as a z-axis. For clarity, it should be remembered that the stent is intended to be folded, perhaps significantly, during use, so that good flexibility is certainly one of the required characteristics. In the embodiments illustrated here, the body of the stent 1 is constituted by a series of successive segments of generally annular form, indicated as 2 in the drawings.

In order to illustrate these ideas, without them being interpreted in a limitative sense in the context of the invention, the length of the segments 2 measured in the longitudinal direction of the stent 1, that is, along the z-axis, is of the order of approximately 2 mm (or several mm). In other words, the segments 2 are usually fairly "short". The various segments of the stent 1 illustrated here are joined together by bridges 3 (which are actually integral components of the stent wall) intended to form a hinge connection between the segments 2 to enable the stent 1 to flex or bend.

Figure 2:
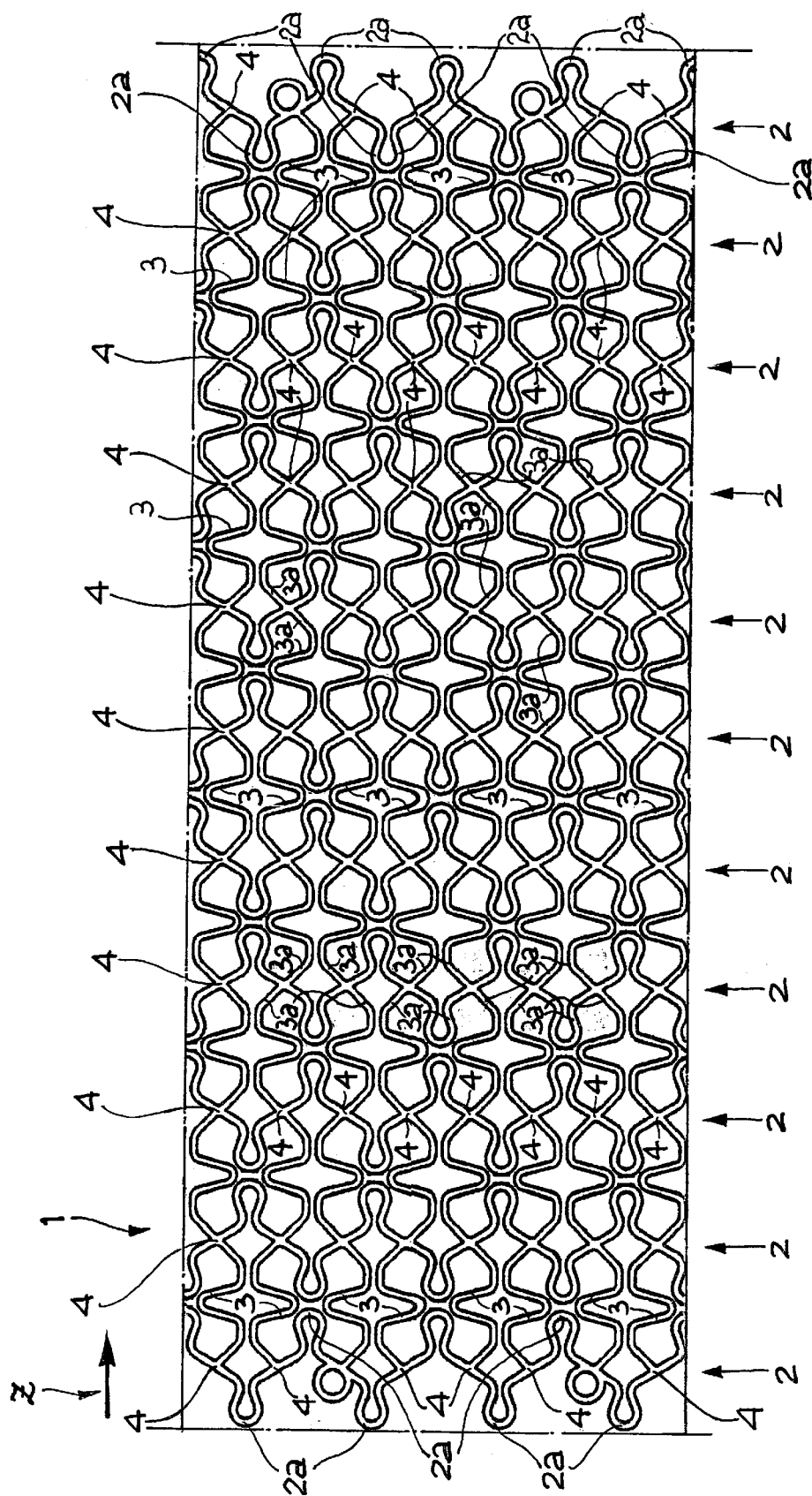
FIG. 2 illustrates, in conditions substantially similar to those of FIG. 1, that is, in the radially-contracted condition, another possible embodiment of the invention.
Figure 3:
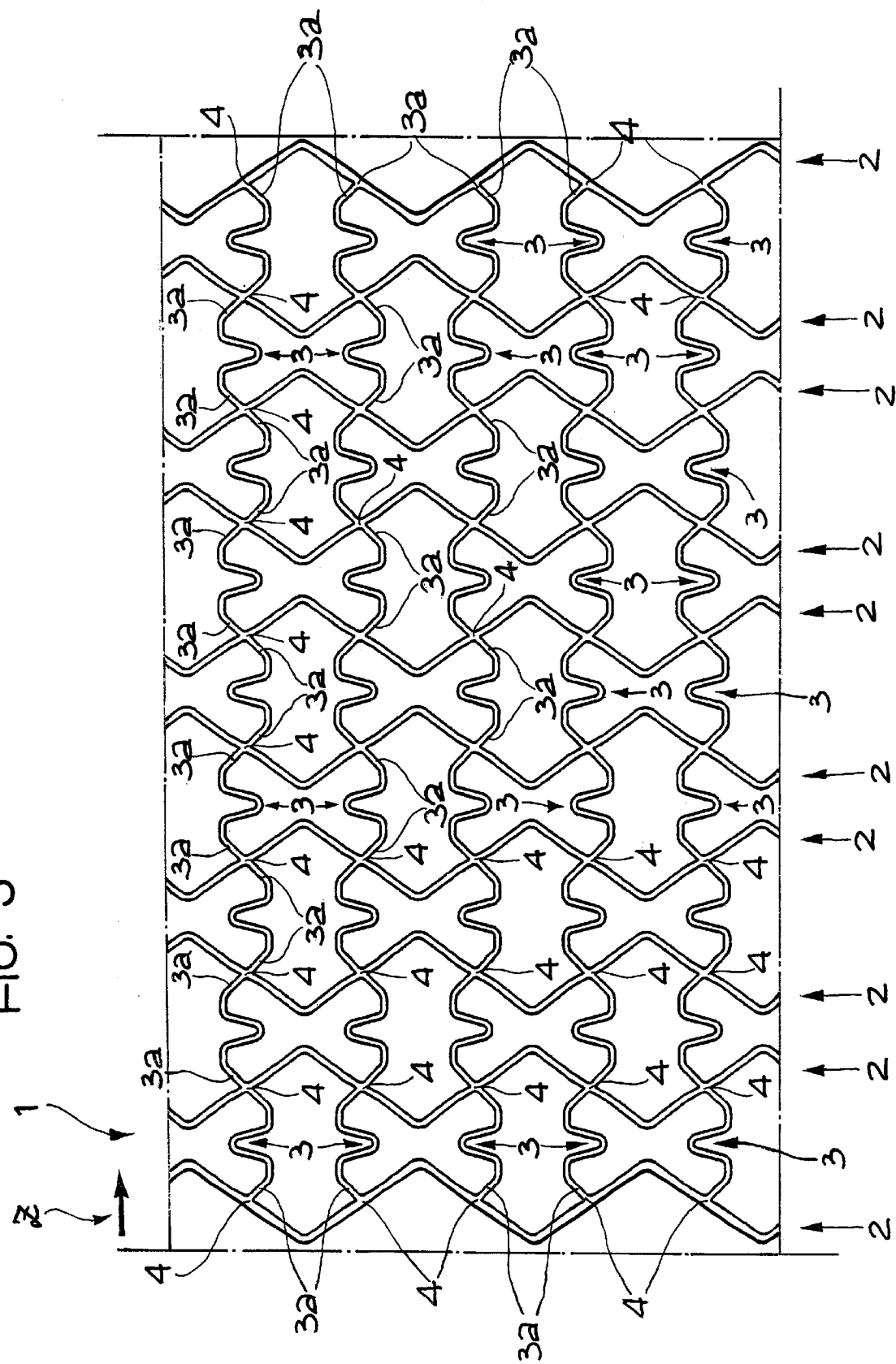
FIG. 3 illustrates, also in a theoretical plane, the geometrical characteristics of the wall of the stent according to FIG. 2 seen in the radially-expanded condition.

Essentially, the longitudinal flexibility of the stent 1, necessary to assist in its location at the implantation site, is essentially due to the bridges 3, while its structural strength, that is, its support of the lumen, is due primarily to the structure of the segments 2 with the co-operation of the bridges 3 being envisaged for this purpose as seen in the embodiment of FIGS. 2 and 3. All this gives rise to the possibility of achieving optimization of the desired characteristics by means of an exact adaptation of the sections of the various component elements.

Examining the structure of FIG. 1 first of all, which is the most simple from this point of view, it can be noted that each segment 2 has a serpentine-like shape with a generally sinusoidal profile.

In the embodiment and the radially-contracted condition illustrated in FIG. 2, the aforesaid serpentine-like shape assumes a more complex shape which may be seen hypothetically as being derived from the shape shown in FIG. 1 due to a "squeezing" of the apex part 2a of each of the half-waves of the sinusoidal path illustrated in FIG. 1 until it achieves an almost lobe-like shape.

In any case, by examining the same structure in the radially-expanded condition illustrated in FIG. 3, it can be noted that the aforesaid serpentine-like shape translates, in this expanded condition, into a triangular wave shape.

Both in the embodiment of FIG. 1, as well as in the embodiment of FIG. 2, the segments 2 have a serpentine-like shape with successive loop parts having a generally opposite concavity.

In each segment 2, the aforesaid loop parts open alternately towards the left and right (with reference to the plane of the drawing in FIGS. 1 and 2) in an arrangement in which the shapes of adjacent segments 2 may be seen, as it were, as opposite in phase (that is, offset by 180°), so that the concavity of each loop faces the concavity of an adjacent segment 2, and the respective convexity faces the convexity of the adjacent segment 2 on the opposite side. The aforesaid loop parts are connected by intermediate connector parts indicated 4.

In the embodiment of FIG. 1, the aforesaid connector parts 4 correspond in practice to the crossings of the zero points of the theoretical sinusoidal path of the segments 2 and extend—when the stent is in the radially-contracted position—substantially in the longitudinal direction of the stent 1, that is, along the z-axis.

In the embodiments of FIGS. 2 and 3, the aforesaid connector parts 4 are also generally straight and extend to connect the loop parts that are crushed or squeezed (as defined above in relation to the stent 1 in the radially-contracted condition, that is, as shown in FIG. 2) in a generally oblique direction, and practically at approximately 45° with respect to the longitudinal axis z of the stent, maintaining this orientation substantially unchanged even during the radial expansion of the stent 1 so that, when the stent is expanded (FIG. 3), the connector parts 4 constitute the central portions of the sides of the triangular wave profile assumed by each segment 2.

Naturally, in consideration of the alternating sequential distribution of the loop parts of the segments 2, the connector parts 4 form, with respect to the aforesaid longitudinal axis z, alternate positive and negative angles (that is, approximately +45°, −45°, +45°, −45° etc. ¼ the sign of the aforesaid angle being in itself irrelevant, in that what counts is the inversion of the sign in the sequence of connector parts 4).

Even though the concept is very clear to the expert in the field, with reference to the plane of the wall of the stent 1 as shown in FIGS. 1 to 3, the radial expansion of the stent corresponds (for example, the embodiments of FIGS. 2 and 3 illustrate both the radially-contracted and the radially-extended positions) to a stretching of the plane represented in FIG. 2 in the sense of an increase in the height, that is, a dilatation in the vertical sense, as represented in FIG. 3.

An important characteristic of the arrangement according to the invention is given by the fact that the bridges 3 connect to the segments 2 not only at the loops thereof, but also at the connector parts 4 and, in particular, at a median position thereof.

Therefore, with reference to the embodiment of FIG. 1, the bridges 3 attach to the segments 2 approximately in correspondence with the zero points of the respective sinusoidal paths.

Since, as has been seen above, when the stent is in the radially-contracted position, the connector parts 4 are oriented along the longitudinal axis z of the stent 1, in the embodiment of FIG. 1 the bridges 3 have generally curved and extended end parts 3a at the end connected to the connector parts 4 in a theoretical transverse plane with respect to the stent 1 (that is, in a generally orthogonal plane with respect to the longitudinal axis z).

The bridges 3 preferably have a curved profile. They also may have a rigid or inflexible median portion. In the embodiments illustrated, the curved profile corresponds substantially to a V-shape. The two branches of the V preferably have distal connector parts at the end regions 3a which extend in an approximately longitudinal direction (z axis) with respect to the stent 1.

The aforesaid V-shape (but a different shape of equivalent concave-convex type can equally well be used within the ambit of the present invention) enables the formation of a very strong connection between adjacent segments of the stent 1. In practice, for each sinusoidal wave of the theoretical path of the segments 2, a bridge 3 can be present for connection to the adjacent segment 2 "to the left", and another bridge 3 for connecting to the adjacent segment 2 "to the right". Naturally, in the case of the segments 2 located at the end of the stent, the above applies to the single adjacent segment 2.

From this arises the possibility of conferring on the wall of the stent 1, which is naturally apertured, a very dense and extremely uniform reticular structure.

In this sense, it can be useful if, for example, in the embodiment of FIG. 1, the rigid parts (that is, in the example illustrated, the V-shape parts) of the bridges 3 are all oriented with their convexity (or concavity) facing in the same direction, so as to enable the possible co-penetration of the extensions of adjacent bridges 3 (that is, with the convex part of one of the bridges 3 penetrating the concave part of the adjacent bridge 3, and thus going beyond the condition of overall tangency adopted in the embodiment shown by way of example in FIG. 1).

In any case, it appears possible to adopt a different solution, for example, with the bridges 3 having their concavity/convexity facing in opposite directions in alternate sequence. As in the case of practically all the other sequences referred to in the present description and in the following claims, it is not necessary to think of an alternating sequence with a single step, as the sequence can be different: for example, two-step, with two bridges 3 having their concavity facing in one direction, followed by two bridges with their concavity facing in the opposite direction, etc.; the entirety following a theoretical path along the circumference of the stent 1.

The embodiment of FIGS. 2 and 3 actually adopts a bridge structure 3 having a general V-shape, single step alternating sequence, with the concavity/convexity of adjacent bridges 3 alternating in the sense of a theoretical path along the periphery of the stent 1.

Due to the generally oblique or inclined orientation of the connector parts 4, the bridges 3 of the embodiment of FIGS. 2 and 3 also have their respective end parts 3a oriented, for example, at an angle of approximately 45°, with respect to the longitudinal axis z of the stent.

This is because the aforesaid end parts 3a connect at the connector parts 4 which extend obliquely, with the terminal parts 3a of the bridges oriented substantially at right angles (that is, at approximately 90°) with respect to the direction in which the connector parts 4 lie.

Looking at the alternating arrangement of the connector parts 4 (for example, in the sequence +45°, −45°, etc. with respect to the z-axis), the end parts 3a of the bridges 3 in FIGS. 2 and 3 show a corresponding orientation.

In general, the bridges 3 connect the same connector parts 4 of a given segment 2 to the immediately adjacent segments which extend between them in a substantially co-linear position.

Consequently, in the zones in which the corresponding bridges attach to the same connector part 4, there is formed a cruciform configuration the arms of which (two constituted by the connector parts 4 and the other two formed by the end parts 3a of the bridges 3 which are joined thereto) are oriented obliquely, usually at approximately 45°, with respect to the longitudinal axis z of the stent.

This configuration and orientation of the aforesaid crosses is maintained practically unchanged during the passage of the stent from the radially-contracted position (FIG. 2) to the radially-extended position (FIG. 3).

To this spatial disposition (maintained during the expansion of the stent) of the cruciform parts is added the fact that, as in the embodiment of FIG. 1, the loop parts of the segments 2 are oriented, in adjacent segments 2, with sequential opposite concavity (or phase opposition, as already said above). Therefore wherever a particular segment 2 has a concavity, the adjacent segment 2 on one side also has a concavity while, wherever the first segment 2 under consideration has a convexity, the adjacent segment 2 on the opposite side also has a convexity. The apex parts (2a) extend along an approximately lobe-shaped path.

During radial expansion of the stent from the contracted condition illustrated in FIG. 2 to the expanded position illustrated in FIG. 3, the wall of the stent passes from the "clover-leaf" configuration theoretically recognisable in FIG. 2 to the reticular structure shown in FIG. 3 in which the stent wall may theoretically be seen as constituted by a succession of approximately quadrangular closed loops (although with a mixtilinear outline), each having a greater dimension, with each loop joining peripherally with four adjacent loops having their greater dimensions oriented at right angles. The connection between adjacent loops occurs at portions of the wall oriented generally at an angle (that is, substantially 45°) to the direction of the longitudinal axis z of the stent.

It is, however, clear that the above detailed description applies to all aspects of the segments 2 and to the bridges 3 included in the body of the stent 1, while in the case of the two segments 2 at the ends of the stent, it is clear that these only have a single adjacent segment 2.

From the embodiment of FIG. 1 can be derived, for example, the fact that the bridges 3 are only present, in the case of the segments 2 at the end positions, in correspondence with the loops the concavity of which faces the interior of the stent, as it is not necessary to provide bridges in correspondence with the loops the concavity of which faces the exterior of the stent 1.

The same discussion applies equally to the embodiments of FIGS. 2 and 3 in which the end portions 3a of the bridges 3 attached to a segment 2 situated at the end position connect with the corresponding connector parts 4, not in a general cruciform conformation, but in a T-shape.

From comparison of FIGS. 2 and 3, it can easily be noted that these T-shape connection zones, just like the cruciform connector parts present in the body of the stent 1, are not subjected to any appreciable rotation when the stent 1 is deployed from the radially-contracted position to the radially-extended position.

Experiments conducted by the Applicant show that this absence of rotation of the connector parts, with a consequent maintenance of the spatial orientation and geometry of the relative zones during the radial expansion of the stent, is advantageous from various points of view, particularly as regards achieving the most regular and uniform expansion possible.

In general, both in the embodiment of FIG. 1 and in the embodiment of FIGS. 2 and 3, the expansion of the stent 1 does not cause appreciable variation in the length (that is, along the z-axis) of the stent 1.

This is because the aforesaid expansion movement affects primarily the loops of the segments 2, while not only are the bridges 3 which substantially define the length of the stent 1 not affected appreciably by the expansion movement, but they connect to the segments 2 precisely in correspondence with the connector parts 4. These constitute, in relation to the segments 2, parts that are not subjected to appreciable movements during the radial expansion of the stent.

Naturally, the principle of the invention remaining the same, the details of construction and the embodiments may be widely varied with respect to those described and illustrated, without by this departing from the ambit of the present invention.

What is claimed is:

1. A stent having a substantially tubular body having a longitudinal axis, the tubular body capable of being dilated from a radially-contracted position to a radially-expanded position comprising:
    a plurality of annular segments having a shape defining a substantially sinusoidal path; and
    at least one bridge connector having an orientation with respect to the longitudinal axis and having a curved portion; the curved portion being connected to first and second connector arms, the connector arms being oriented in an oblique configuration with respect to the curved portion, the connector arms having first and second ends, respectively, the first end extending obliquely from the first connector arm and the second end extending obliquely from the second connector arm, the first end connected to a first annular segment and the second end connected to a second adjacent annular segment, wherein adjacent curved portions have opposite, sequential convexity.

2. The stent according to claim 1, further wherein the orientation of the bridge connector with respect to the longitudinal axis remains substantially unchanged as the tubular body is expanded from the contracted to the expanded position.

3. The stent according to claim 1, wherein the connector arms are substantially parallel to the longitudinal axis when the tubular body is in the contracted position and when the tubular body is in the expanded position.

4. The stent according to claim 1, wherein adjacent curved portions have sequential convexity.

5. The stent according to claim 1, wherein the curved portion has a V-shape.

6. The stent according to claim 1, wherein the first and second ends of the bridge connectors join successive annular segments to form a cross-shape configuration.

7. A stent having a substantially tubular body having a longitudinal axis, the tubular body capable of being dilated from a radially-contracted position to a radially-expanded position comprising:
    a plurality of annular segments having a shape defining a substantially sinusoidal path; and
    at least one bridge connector having a curved portion, the curved portion having first and second branches, the first branch being connected in a non-linear configuration to a first connector arm, the second branch being connected in a non-linear configuration to a second connector arm, the connector arms having first and second ends, respectively, the first and second ends being configured to form first and second angles with respect to the first and second connector arms, respectively, the first and second angles being non-zero, the first end connected to a first annular segment and the second end connected to a second adjacent annular segment, wherein adjacent curved portions have opposite, sequential convexity.

8. The stent according to claim 7, wherein adjacent curved portions have sequential convexity.

9. The stent according to claim 7, wherein the curved portion has a V-shape.

10. The stent according to claim 7, wherein at least one of the first and second ends are joined to the annular segment in a generally oblique direction with respect to the longitudinal axis of the stent.

11. The stent according to claim 7, wherein the first and second ends of the bridge connectors join successive annular segments to form a substantially cross-shape configuration.

12. A stent having a substantially tubular body having a longitudinal axis, the tubular body capable of being dilated from a radially-contracted position to a radially-expanded position comprising:

a plurality of annular segments having a shape defining a substantially sinusoidal path;

at least one bridge connector having a curved portion; the curved portion being connected to first and second connector arms that are substantially parallel to the longitudinal axis, the first and second connector arms having first and second ends, respectively, the first end extending in a first direction, the second end extending in a second direction, the first and second directions being substantially perpendicular to the longitudinal axis, the first end connected to a first annular segment and the second end connected to a second adjacent annular segment, adjacent curved portions having opposite, sequential convexity, the first and second ends being connected at a point on the annular segments substantially coinciding with zero points of the sinusoidal path defined by the segments, and the orientation of the bridge connector with respect to the longitudinal axis remaining substantially unchanged as the tubular body is expanded from the contracted to the expanded position.

13. The stent according to claim 12, wherein adjacent bridge connectors have sequential convexity.

14. The stent according to claim 12, wherein the curved portion is a V-shape.

15. The stent according to claim 12, wherein at least one of the first and second ends are joined to the annular segment in a generally oblique direction with respect to the longitudinal axis of the stent.

16. The stent according to claim 12, wherein the first and second ends of the connector arms join successive annular segments in a general cross-shape.

17. A method of preventing restenosis of a vessel comprising:

providing a stent having a substantially tubular body having a longitudinal axis, the tubular body capable of being dilated from a radially-contracted position to a radially-expanded position, the tubular body comprising a plurality of annular segments having a shape defining a substantially sinusoidal path, at least one bridge connector having a curved portion; the curved portion being connected to first and second connector arms, the connector arms being oriented in an oblique configuration with respect to the curved portion, the connector arms having first and second ends, respectively, the first end extending obliquely from the first connector arm and the second end extending obliquely from the second connector arm, the first end connected to a first annular segment and the second end connected to a second adjacent annular segment, adjacent bridge connectors having opposite, sequential convexity;

advancing the tubular body in the contracted condition through the lumen of the vessel to an area of stenosis; and deploying the tubular body within the lumen of the vessel by expanding it from the contracted to the expanded condition.

18. The method according to claim 17, wherein the step of providing a bridge connector having a curved profile comprises providing adjacent bridge connectors having sequential convexity.

19. The method according to claim 17, wherein the step of providing the stent further comprises providing a curved portion having a V-shape.

20. The method according to claim 17, wherein the step of providing the stent further comprises providing a bridge connector wherein the first and second ends join successive annular segments to form a substantially cross-shape configuration.

21. A method of making a stent having a substantially tubular body defining a longitudinal axis, the method comprising:

providing a tubular blank; and forming the blank into a plurality of annular segments joined by at least one bridge connector, the annular segments having a shape defining a substantially sinusoidal path, wherein at least one bridge connector comprises a curved portion connected to first and second connector arms that are substantially parallel to the longitudinal axis, the first and second connector arms having first and second ends, respectively, the first end extending in a first direction, the second end extending in a second direction, the first and second directions being substantially perpendicular to the longitudinal axis, the first end connected to a first annular segment and the second end connected to a second adjacent annular segment, the curved portion of adjacent bridge connectors having opposite, sequential convexity, the first and second ends being connected at a point on the annular segments substantially coinciding with zero points of the sinusoidal path defined by the segments.

22. The method according to claim 21, wherein the forming step is by a method selected from one of laser incision, photo-incision, and electroerosion.

23. The method according to claim 21, wherein the forming step further comprises adjacent bridge connectors having sequential convexity.

24. The method according to claim 21, wherein the forming step further comprises forming the blank such that the curved portion of the bridge connector has a V-shape.

25. The method according to claim 21, wherein the forming step further comprises forming the blank such that at least one of the first and second ends of the connector arms are joined to the annular segment in a generally oblique direction with respect to the longitudinal axis of the stent.

26. The method according to claim 21, wherein the forming step further comprises forming the blank such that the first and second ends of the bridge connector join successive annular segments to form a substantially cross-shape configuration.

27. A stent having a substantially tubular body having a longitudinal axis, the tubular body capable of being dilated from a radially-contracted position to a radially-expanded position comprising:

a plurality of annular segments having a shape defining a substantially sinusoidal path; and at least one bridge connector having an orientation with respect to the longitudinal axis and having a curved portion; the curved portion being connected to first and second connector arms, the connector arms being oriented in an oblique configuration with respect to the curved portion, the connector arms having first and second ends, respectively, the first end extending obliquely from the first connector arm and the second end extending obliquely from the second connector arm, the first end connected to a first annular segment and the second end connected to a second adjacent annular segment, wherein the first and second ends are connected at a point on the annular segments substantially coinciding with zero points of the sinusoidal path defined by the segments and further wherein the shape of the bridge connector remains substantially unchanged as the tubular body is expanded from the contracted to the expanded condition.

28. A stent having a substantially tubular body having a longitudinal axis, the tubular body capable of being dilated from a radially-contracted position to a radially-expanded position comprising:

a plurality of annular segments having a shape defining a substantially sinusoidal path; and at least one bridge connector having an orientation with respect to the longitudinal axis and having a curved portion; the curved portion being connected to first and second connector arms, the connector arms being oriented in an oblique configuration with respect to the curved portion, the connector arms having first and second ends, respectively, the first end extending obliquely from the first connector arm and the second end extending obliquely from the second connector arm, the first end connected to a first annular segment and the second end connected to a second adjacent annular segment, wherein the first and second ends of the bridge connectors join successive annular segments to form a T-shape configuration.

29. A stent having a substantially tubular body having a longitudinal axis, the tubular body capable of being dilated from a radially-contracted position to a radially-expanded position comprising:

a plurality of annular segments having a shape defining a substantially sinusoidal path; and at least one bridge connector having a curved portion, the curved portion having first and second branches, the first branch being connected in a non-linear configuration to a first connector arm, the second branch being connected in a non-linear configuration to a second connector arm, the connector arms having first and second ends, respectively, the first and second ends being configured to form first and second angles with respect to the first and second connector arms, respectively, the first and second angles being non-zero, the first end connected to a first annular segment and the second end connected to a second adjacent annular segment, wherein the first and second ends are connected at a point on the annular segments substantially coinciding with zero points of the sinusoidal path defined by the segments, the annular segments and bridge connectors defining an angular configuration with respect to the longitudinal axis which remains substantially unchanged as the tubular body is expanded from the contracted to the expanded condition.

30. A stent having a substantially tubular body having a longitudinal axis, the tubular body capable of being dilated from a radially-contracted position to a radially-expanded position comprising:

a plurality of annular segments having a shape defining a substantially sinusoidal path; and at least one bridge connector having a curved portion, the curved portion having first and second branches, the first branch being connected in a non-linear configuration to a first connector arm, the second branch being connected in a non-linear configuration to a second connector arm, the connector arms having first and second ends, respectively, the first and second ends being configured to form first and second angles with respect to the first and second connector arms, respectively, the first and second angles being non-zero, the first end connected to a first annular segment and the second end connected to a second adjacent annular segment, wherein the first and second ends of the bridge connectors join successive annular segments to form a T-shape configuration.

31. A method of preventing restenosis of a vessel comprising:

providing a stent having a substantially tubular body having a longitudinal axis, the tubular body capable of being dilated from a radially-contracted position to a radially-expanded position, the tubular body comprising a plurality of annular segments having a shape defining a substantially sinusoidal path, at least one bridge connector having a curved portion; the curved portion being connected to first and second connector arms, the connector arms being oriented in an oblique configuration with respect to the curved portion, the connector arms having first and second ends, respectively, the first end extending obliquely from the first connector arm and the second end extending obliquely from the second connector arm, the first end connected to a first annular segment and the second end connected to a second adjacent annular segment, the bridge connector joining successive annular segments at first and second joints, the first and second joints each forming a T-shape configuration;

advancing the tubular body in the contracted condition through the lumen of the vessel to an area of stenosis; and deploying the tubular body within the lumen of the vessel by expanding it from the contracted to the expanded condition.

32. A method of making a stent having a substantially tubular body defining a longitudinal axis, the method comprising:

providing a tubular blank; and forming the blank into a plurality of annular segments joined by at least one bridge connector, the annular segments having a shape defining a substantially sinusoidal path, wherein at least one bridge connector comprises a curved portion connected to first and second connector arms that are substantially parallel to the longitudinal axis, the first and second connector arms having first and second ends, respectively, the first end extending in a first direction, the second end extending in a second direction, the first and second directions being substantially perpendicular to the longitudinal axis, the first end connected to a first annular segment and the second end connected to a second adjacent annular segment, the first and second ends of the bridge connector joining successive annular segments to form a T-shape configuration and the first and second ends being connected at a point on the annular segments substantially coinciding with zero points of the sinusoidal path defined by the segments.

33. A stent having a substantially tubular body having a longitudinal axis, the tubular body capable of being dilated from a radially-contracted position to a radially-expanded position comprising:

a plurality of annular segments having a shape defining a substantially sinusoidal path; and at least one bridge connector having first and second end portions, first and second intermediate portions, and a curved mid-portion having first and second branches, the first end portion, first intermediate portion and first branch forming a first side of the connector and the second end portion, second intermediate portion, and second branch forming a second side of the connector, the first end portion connected to a first annular segment and the second end portion connected to a second adjacent annular segment, the connector being configured such that the first end portion, first intermediate portion, and first branch extend in first, second, and third directions, respectively, the second direction being non-linear with respect to the first and third directions, and the second end portion, second intermediate portion, and second branch portion extending in fourth, fifth and sixth directions, respectively, the fifth direction being non-linear with respect to the fourth and sixth directions; wherein the first and second end portions are connected at a point on the annular segments substantially coinciding with zero points of the sinusoidal path defined by the segments.

34. The stent of claim 33 wherein the curved portion is substantially a V-shape.

35. The stent of claim 33 wherein the connector is configured such that the first end portion, first intermediate portion, and first branch are substantially symmetric with the second end portion, second intermediate portion, and second branch about a plane orthogonal to the longitudinal axis and intersecting an apex of the V-shaped mid portion.

* * * * *